United States Patent
Hasenböhler et al.

(10) Patent No.: US 8,403,972 B2
(45) Date of Patent: Mar. 26, 2013

(54) THREAD-FORMING SCREW

(75) Inventors: Alain Hasenböhler, Binningen (CH);
Peter Scheuble, Schliengen (DE); Dirk Thiel, Staufen (DE)

(73) Assignee: Medartis AG, Basel (CH)

( * ) Notice: Subject to any disclaimer, the term of this patent is extended or adjusted under 35 U.S.C. 154(b) by 417 days.

(21) Appl. No.: 12/091,137

(22) PCT Filed: Oct. 25, 2006

(86) PCT No.: PCT/CH2006/000597
§ 371 (c)(1),
(2), (4) Date: Aug. 13, 2008

(87) PCT Pub. No.: WO2007/048267
PCT Pub. Date: May 3, 2007

(65) Prior Publication Data
US 2008/0292429 A1 Nov. 27, 2008

(30) Foreign Application Priority Data
Oct. 28, 2005 (CH) ..................................... 1731/05

(51) Int. Cl.
*A61B 17/04* (2006.01)

(52) U.S. Cl. ......................... 606/309; 411/411
(58) Field of Classification Search .................. 411/411, 411/412, 415, 424, 426; 606/301, 315, 316, 606/317; 433/172–176, 201.1
See application file for complete search history.

(56) References Cited

U.S. PATENT DOCUMENTS

| 3,454,070 | A | * | 7/1969 | Phipard, Jr. | 411/168 |
| 6,001,101 | A | * | 12/1999 | Augagneur et al. | 606/316 |
| 6,030,162 | A | * | 2/2000 | Huebner | 411/413 |
| 6,306,140 | B1 | * | 10/2001 | Siddiqui | 606/315 |
| 2003/0120279 | A1 | | 6/2003 | Hansson | |
| 2003/0153919 | A1 | * | 8/2003 | Harris | 606/69 |
| 2004/0230195 | A1 | * | 11/2004 | Kaikkonen et al. | 606/72 |
| 2005/0038438 | A1 | * | 2/2005 | Anderson et al. | 606/73 |
| 2005/0101961 | A1 | * | 5/2005 | Huebner et al. | 606/72 |
| 2005/0163596 | A1 | * | 7/2005 | Ho | 411/411 |
| 2007/0147973 | A1 | * | 6/2007 | Laan | 411/411 |

FOREIGN PATENT DOCUMENTS

| DE | 20 2004 011 145 | 11/2004 |
| FR | 2 808 182 | 11/2001 |
| WO | WO 2004/086991 A1 | 10/2004 |

OTHER PUBLICATIONS

International Search Report issued in related International Application No. PCT/CH2006/000597 on Jan. 25, 2007.

* cited by examiner

*Primary Examiner* — Nicholas Woodall
*Assistant Examiner* — Melissa A Hall
(74) *Attorney, Agent, or Firm* — Brinks Hofer Gilson & Lione

(57) ABSTRACT

A thread-forming screw includes a screw end, a shank, and a thread-free head, wherein the shank is provided at least partly with a thread and has a pre-forming region, an intermediate region, which is arranged to follow the pre-forming region, and an anchoring region, which is arranged so as to adjoin the intermediate region and below the head, wherein the pre-forming region is arranged so as to directly adjoin the screw end.

11 Claims, 17 Drawing Sheets

THREAD-FORMING SCREW

BACKGROUND OF THE INVENTION

The invention relates to a thread-forming screw, and in particular a bone screw.

Thread-forming screws are widely known in the form of self-tapping or self-drilling screws. They have the advantage that no thread has to be precut. Such a screw is known, for example, from DE 20 2004 011 145 U1 and is used there as a masonry screw, for example as a brick screw. The screw described there has a preforming region with a pilot thread, adjoining which is a first thread section, then a threadless section and then at least one further thread section which is arranged below the screw thread.

Self-tapping and self-drilling screws are also used in other fields, for example in medical engineering, and here in particular in the area of osteosynthesis (for example in the skull area, in the oral and maxillofacial area, in the hand area or in trauma surgery). The screws used in this case are screws whose shanks are of cylindrical or conical design over the entire shank length (with the exception of the pointed or blunt screw end) and which are provided with a continuous thread of constant pitch. Aids which are indispensable in osteosynthesis, such as, for example, bone plates or plates of distractors, are fastened by means of these screws.

In applications in the skull area or especially in the oral and maxillofacial area, the diameters of such screws are of course as small as possible. However, since the screws have to be fixedly anchored in the bone, they often have a not inconsiderable shank since the screws have to be fixedly anchored in the bone, they often have a not inconsiderable shank length, even more so when a transmucosal or transgingival fastening is considered and it is thus desired to avoid a surgical preparation of the bone (by cutting open or lifting away mucosa or gingiva).

However, some difficulties may occur when screwing in such screws. For example, the torque increases quite considerably with increasing screw-in depth, which in particular in the case of longer screws requires the application of quite considerable forces by the surgeon, and that in a typically very restricted operating zone. This applies both to self-tapping screws, for which a core hole is produced beforehand in the bone in a separate step, and even more so to self-drilling screws, which are screwed without pilot holes into the bone, which saves a processing step (namely the pilot drilling) for the surgeon and can even lead to better anchoring of the screw in the bone.

In addition, when applying the requisite torques, which become higher and higher with increasing screw-in depth, the relatively thin screw shank may break (torsion fracture), such that the rest of the screw shank already in the bone has to be removed in a complicated manner in such a case. This can certainly be prohibited somewhat in the case of self-tapping screws by increasing the diameter of the core hole. To this end, however, either a further processing step is required (opening out the original core hole using a drill bit of larger diameter) or drilling is carried out immediately with a drill bit of larger diameter, there then being the risk of getting the drill bits mixed up and of not drilling with the correct drill bit. In addition, the anchoring of the screw in the bone in the case of a larger diameter of the core hole is of course slightly poorer.

Both the additional processing step of the further pilot drilling and the risk of mix-up when selecting the drill bit and also the application of partly very high forces for producing the requisite torque are disadvantageous for surgeons. The present invention comes in here, the object of which is to propose a screw which can provide a remedy in this respect.

SUMMARY

Specifically, a thread-forming screw, in particular a bone screw, is proposed, having a screw end, a shank and a thread-free head. The shank is provided at least partly with a thread and has a preforming region, an intermediate region, which is arranged to follow the preforming region, and an anchoring region. The anchoring region is arranged so as to adjoin the intermediate region and below the head. The preforming region is arranged so as to directly adjoin the screw end. When the preforming region is being screwed in, the torque required for the screwing-in increases until the preforming region of the screw has been completely screwed in. The preforming region, the intermediate region and the anchoring region are designed in such a way that, after the preforming region has been completely screwed in, there is either no increase in the torque required for the screwing-in or there is only a slight increase in the requisite torque, in relation to the increase during the screwing-in of the preforming region, until the screw is screwed in right up to its anchoring region. The expression "no increase in the torque" is intended here to also include those cases in which the requisite torque can not only remain the same but can even decrease when the screw is screwed in further. This may be the case, for example, when the preforming region has been screwed through the cortical substance and penetrates into the spongiosa. For the further screwing of the preforming region into the spongiosa, a lower torque than when screwing into the cortical substance then has to be applied. The intermediate region of the screw can likewise be screwed into the cortical substance with a lower torque than the preforming region, such that the sum of the requisite torques for the screwing-in of the preforming region and of the intermediate region in such a case can be lower than the torque which is required for screwing the preforming region into the cortical substance.

As a result, the screw according to the invention differs substantially from conventional screws: depending on how the screw is designed, the screw-in torque remains essentially constant after the preforming region has been screwed in (the preforming region extending only over part of the length of the screw shank), and therefore no substantial increase in the requisite torque takes place. In some cases (see above) the requisite torque can even decrease. Or else the requisite torque can also increase (pronounced cortical substance), but the increase in the requisite torque is always considerably less than the increase in the torque when screwing in conventional screws. The screw length therefore has no effect or only a substantially reduced effect on the requisite screw-in torque, for which reason long self-drilling screws can also be used without there being the risk of breaking (torsion fracture). Pilot drilling for long self-drilling screws for reducing the risk of a torsion fracture is therefore no longer necessary. The screw according to the invention can also be suitable for being produced from bioresorbable materials, which cannot transmit torque of just any desired magnitude.

When the anchoring region is being screwed in, the requisite torque can increase to a more pronounced extent again. However, that is not so critical with regard to the risk of a torsion fracture, because the core diameter in the anchoring region of the screw is regularly of sufficient size in order to be able to reliably transmit the requisite torque.

In an exemplary embodiment of the screw according to the invention, the outside diameter of the screw in the preforming region, at least in a section adjoining the intermediate region, is larger than in the intermediate region itself. In addition, the outside diameter at least in part of the anchoring region is the same size as or essentially the same size as the outside diameter of that section of the preforming region which adjoins the intermediate region.

Since the outside diameter of the preforming region is larger than the outside diameter of the intermediate region where the preforming region adjoins the intermediate region, the intermediate region, depending on how the intermediate region is designed, runs free or the friction during the screwing-in is considerably reduced. For example, it is conceivable to design the intermediate region entirely without a thread and to provide a core diameter which is somewhat smaller than the core diameter of the preforming region where the latter adjoins the intermediate region. The intermediate region can then run free during the screwing-in and there is no increase in the torque. However, the screw then has no hold at all in the bone in the intermediate region. If a thread is likewise provided in the intermediate region, but with a smaller outside diameter than in the preforming region (where the latter adjoins the intermediate region), an additional screw-in torque may become necessary when the screw is being screwed in. However, the increase in the screw-in torque is substantially less than in the case of conventional screws. Instead, the screw also has a better hold in the bone and offers, for example, resistance to being pulled out axially. In addition, the bone can grow into the thread root between the thread crests during the healing process, a factor which further improves the anchoring of the screw in the bone.

In a further embodiment of the screw according to the invention, the screw end is of blunt design. This screw is therefore a self-tapping (not self-drilling) screw; a pilot hole is therefore produced in the bone before the self-tapping screw is then screwed into this pilot hole and the thread cuts into the bone. The outside diameter of the screw is constant in the preforming region (cylindrical preforming region). In the intermediate region, it is smaller in a section directly adjoining the preforming region than the outside diameter of the preforming region. Starting from this section of the intermediate region adjoining the preforming region, the outside diameter increases conically across the intermediate region and the anchoring region until, in the anchoring region, it is the same size as or larger than the outside diameter of the preforming region. That is to say that, after the preforming region has been screwed in, at most only a torque which is substantially lower than in conventional screws has to be applied during the further screwing-in. At the end of the screw-in operation, the anchoring region of the screw comes to lie in the cortical substance, and, since at least part of the anchoring region has an outside diameter which is the same size as or essentially the same size as the preforming region, the screw is then effectively anchored in the cortical substance.

In another embodiment of the screw according to the invention, the screw end is designed as a point. The screw in this exemplary embodiment is a self-drilling (and of course also self-tapping) screw. A pilot hole does not have to be produced in the bone here—in contrast to the merely self-tapping screw. The outside diameter of the preforming region increases starting from the point up to that section which directly adjoins the intermediate region. In the intermediate region, the outside diameter is smaller in a section directly adjoining the preforming region than the outside diameter of the adjoining section of the preforming region. Starting from this section of the intermediate region adjoining the preforming region, the outside diameter increases conically across the intermediate region and the anchoring region until, at least in part of the anchoring region, it is the same size as or essentially the same size as the outside diameter of the preforming region in the section adjoining the intermediate region.

Due to the point and the at first small diameter of the preforming region, the self-drilling screw can be readily positioned and can also be screwed in very easily at the start of the screwing-in in order to prevent slipping of the screw. With the increase in the outside diameter of the preforming region, the torque to be applied also increases until the preforming region has been completely screwed in. After the preforming region has been completely screwed in, the torque to be applied increases at most to a substantially smaller extent than in conventional screws during the further screwing-in, since there is no complete contact with the bone in the intermediate region and therefore the additional friction is also lower. At the end of the screw-in operation, the anchoring region of the screw comes to lie in the cortical substance, and, since at least part of the anchoring region has an outside diameter which is the same size as or essentially the same size as the preforming region, the screw is then effectively anchored in the cortical substance.

In a further embodiment of the screw according to the invention, the screw shank in the preforming region has a polygon-like cross section which has points or regions which are at a maximum radial distance from the screw axis and regions which are at a smaller radial distance from the screw axis than those points or regions which are at a maximum radial distance from the screw axis. During the preforming of the thread, the friction during the thread forming will therefore always be at a maximum at the points or regions which are at a maximum distance from the screw axis, whereas it becomes lower in the regions lying in between. As a result, the friction required for the screwing-in of the preforming region is reduced once again. For example, the screw shank in the preforming region may be designed as a "curve of constant diameter" which has a triangle-like external form (explained in more detail later).

As already mentioned further above, the outside diameter in the intermediate region, in an exemplary embodiment of the screw according to the invention, is smaller than in that section of the preforming region which adjoins the intermediate region. To this end, for example, the core diameter of the screw shank may be smaller in the intermediate region than in that section of the preforming region which adjoins the intermediate region. However, it should be noted here that the core diameter cannot be selected to be as small as desired just in order to be able to screw in the intermediate region as simply as possible. Care should be taken instead to ensure that the reduced core diameter in the intermediate region—in particular at the transition to the preforming region—is always selected in such a way that the torque required for the screwing-in is also transmitted by the weakest point of the screw in order to reliably prevent breaking (torsion fracture) of the screw. In that part of the anchoring region whose outside diameter is the same size as or essentially the same size as that section of the preforming region which adjoins the intermediate region, the core diameter of the screw shank is the same size as or essentially the same size as the core diameter of that section of the preforming region which adjoins the intermediate region, such that the screw is then effectively anchored in the cortical substance.

In another exemplary embodiment of the screw according to the invention, the screw shank has a constant outside diameter in the preforming region and in the intermediate region. In the preforming region it is provided with a thread having different pitches, namely a first pitch and a second pitch, the second pitch being larger than the first pitch. In the anchoring region—and preferably also in the intermediate region—the screw shank is provided with a thread having a third pitch which is larger than the first pitch and smaller than the second pitch of the thread in the preforming region. During the screwing-in, the thread which is cut by the first thread pitch is subsequently "opened out" slightly (widened in the axial direction) by the second (larger) thread pitch. The following thread turns having the third pitch then come to lie in this widened thread turn; they thus have a slight clearance in the axial direction, for which reason the additional friction is at most low during the screwing-in.

The screw according to the invention is preferably produced from a biocompatible material, for example titanium or a titanium alloy, or from a bioresorbable material (subsequent unscrewing of the screw no longer necessary), which above all is important when it is used as a bone screw and therefore has to be produced from a material well-tolerated in bioapplications. However, this is not the only conceivable field of application, and therefore the material does not absolutely have to be well-tolerated by the body.

Further advantageous aspects of the screw according to the invention follow from the description below of exemplary embodiments of the invention with reference to the drawing.

BRIEF DESCRIPTION OF THE DRAWINGS

FIG. 5 shows a schematic illustration of various positions of the screw from FIG. 1 during the screwing-in;

FIG. 11 shows a schematic illustration of various positions of the screw from FIG. 6 during the screwing-in;

FIG. 16 shows a schematic illustration of various positions of the screw from FIG. 12 during the screwing-in;

DETAILED DESCRIPTION OF THE PREFERRED EMBODIMENTS

Figure 1:
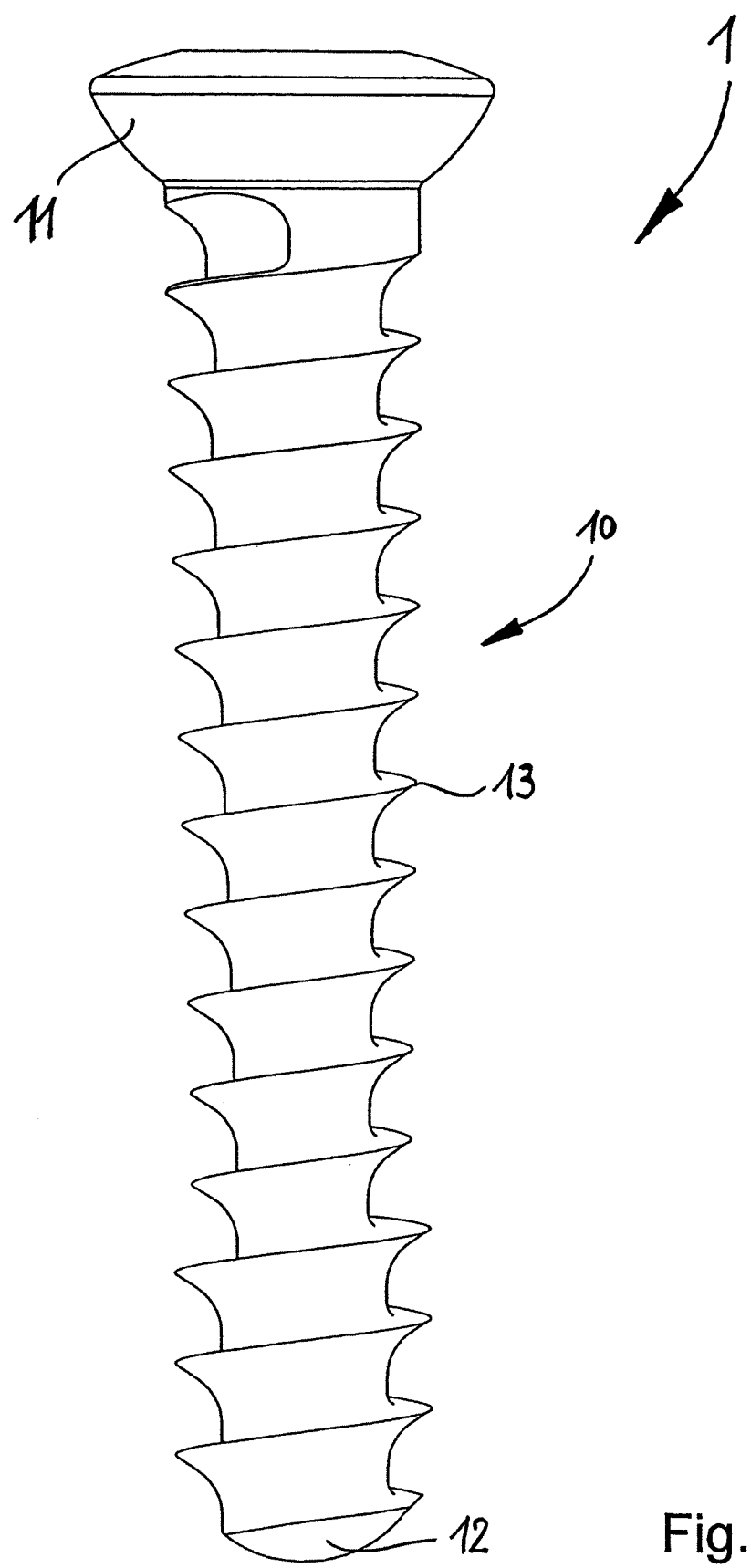
FIG. 1 shows a view of a first exemplary embodiment of the screw according to the invention.
Figure 2:
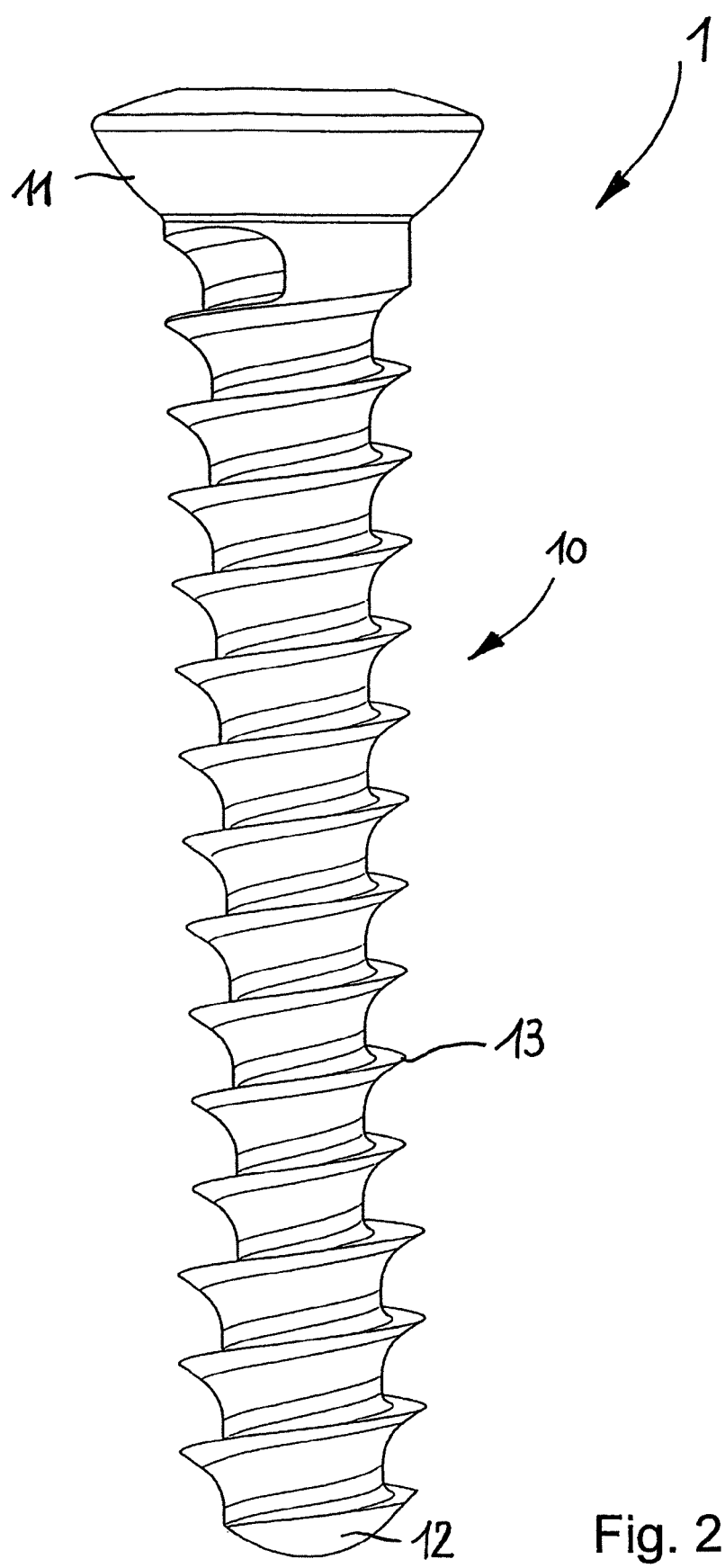
FIG. 2 shows the view from FIG. 1 with some auxiliary lines for better three-dimensional illustration of the screw.

A first exemplary embodiment of the screw according to the invention is explained below with reference to FIGS. 1 to 5. FIG. 1 shows a view of the first exemplary embodiment of the screw according to the invention, here a bone screw. The screw 1 comprises a shank 10 and a thread-free spherical head 11, which, for example, enables it to be accommodated in a countersunk plate hole of a bone plate (not shown). The screw end 12 is of blunt design; the screw 1 shown in FIG. 1 is therefore a self-tapping (not self-drilling) screw. FIG. 2 shows the same screw as FIG. 1, but with some additional auxiliary lines, thereby providing a better three-dimensional impression of the screw 1.

Figure 3:
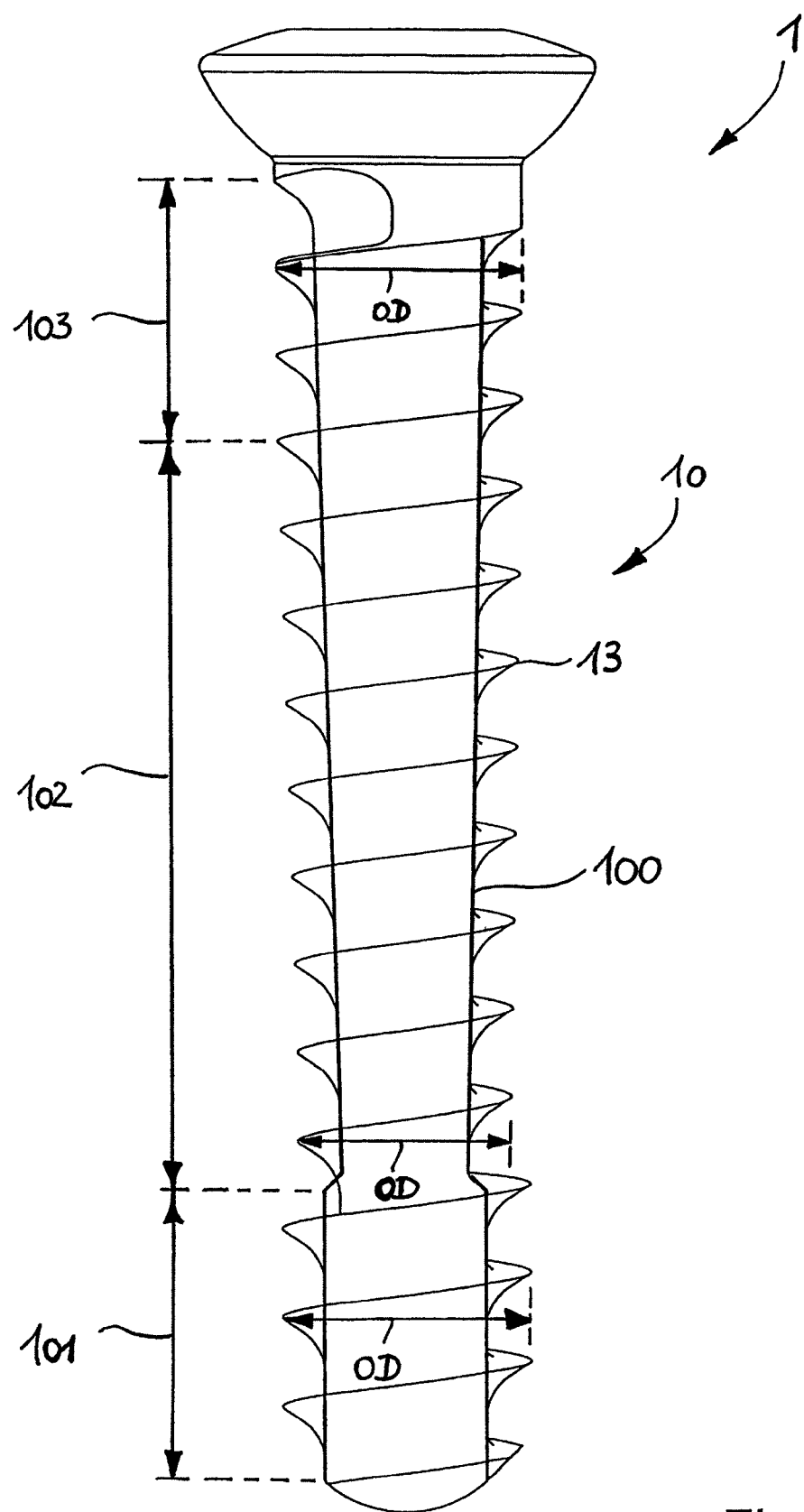
FIG. 3 shows a schematic illustration of the screw from FIG. 1 with exaggerated representation of the core of the screw shank.

The envelope over the thread 13 of the screw, which is designed here as a continuous thread of constant pitch, can be imagined with reference to FIG. 3, although in FIG. 3 only the core 100 of the shank 10 is shown, in exaggerated representation. However, since the thread 13 has a constant radial thread depth, the envelope (not shown), which represents the outside diameter of the screw, runs parallel to the core 100 of the shank 10 over the entire thread 13. The core 100 alone is shown schematically once again in FIG. 4.

The shank 10 has three regions: a preforming region 101, an intermediate region 102 and an anchoring region 103, which regions can best be seen in the illustration in FIG. 3. In this exemplary embodiment, the preforming region 101 is of cylindrical design, such that the outside diameter OD of the screw 1 (the radial thread depth is of course constant) in the entire preforming region 101 is constant. In the directly adjoining section of the intermediate region 101, the outside diameter OD is smaller than in the preforming region 101. Starting from this section of the intermediate region 102 adjoining the preforming region 101, the outside diameter OD increases conically across the intermediate region 102 and the anchoring region 103 until it is almost the same size as in the preforming region 101 at the start of the anchoring region 103 and is the same size as in the preforming region 101 at the top end of the anchoring region 103.

Figure 4:
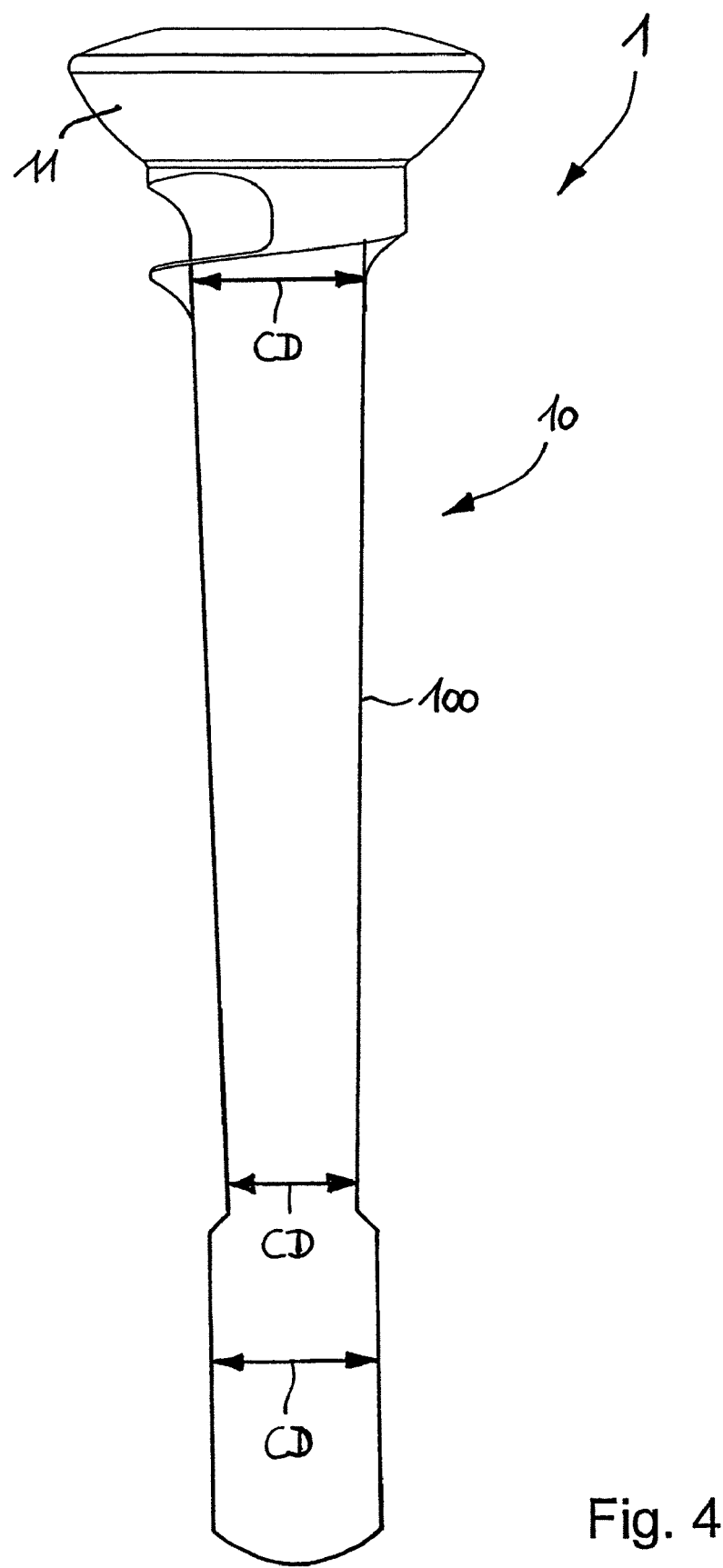
FIG. 4 shows a schematic illustration of the core of the screw shank of the screw from FIG. 1.

This analogously applies to the core diameter CD of the shank 10 (see FIG. 4). The core diameter CD is larger in the preforming region than in the directly adjoining section of the intermediate region, and starting from there it increases conically across the intermediate region and the anchoring region.

Figure 5:
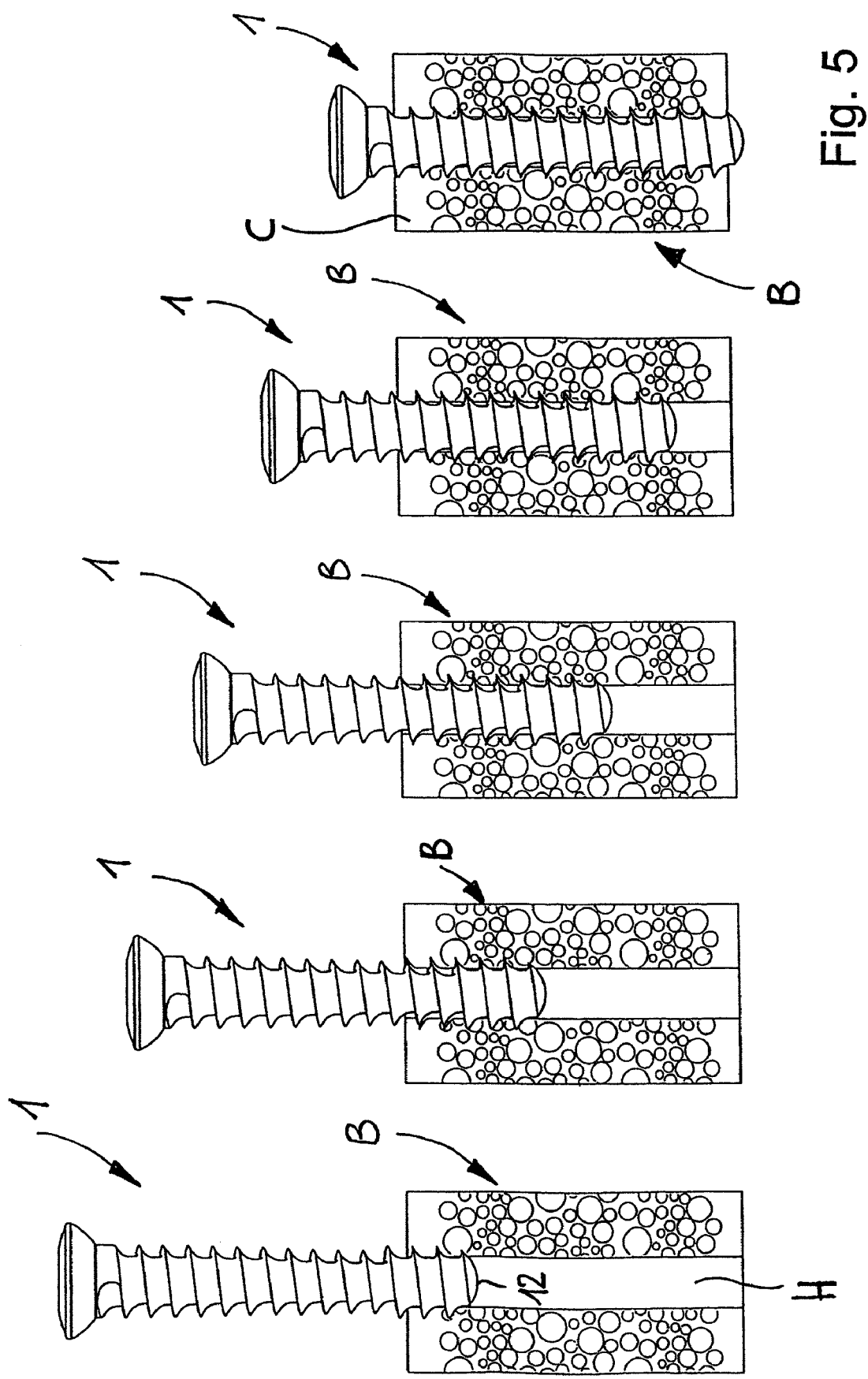

To screw in such a screw 1, which is self-tapping (but not self-drilling), the procedure is as shown in FIG. 5. First of all a (pilot) hole H is produced, the hole diameter of which is of course smaller than the outside diameter of the screw 1, but is larger than the core diameter of the screw 1 in its preforming region 101. The screw 1 is then inserted with the blunt screw end 12 into the hole H, and the preforming region 101 is successively screwed into the bone B (left-hand image in FIG. 5), first of all into the cortical substance. During the screwing-in, a bone thread is formed in the bone B ("cut" into the bone; self-tapping). Once the preforming region 101 has been screwed completely into the bone B, the directly adjoining section of the intermediate region 102 than plunges into the bone B. Since the outside diameter OD of the preforming region 101 is larger than the outside diameter OD of the directly adjoining section of the intermediate region 102, the bone thread cut by the preforming region 101 also has a diameter which is larger than the outside diameter OD of the screw in the intermediate region 102. There is therefore a radial clearance (second image from the left in FIG. 5) between the thread of the intermediate region 102 and the bone thread cut by the preforming region 101. Although the thread flanks can possibly rub slightly in the axial direction on the bone thread cut by the preforming region 101, the thread runs free in the radial direction in the intermediate region. Since the outside diameter of the screw 1 of the intermediate region increases conically, this radial clearance becomes smaller again when the screw 1 is screwed further into the bone B (third and fourth image from the left in FIG. 5). If the screw 3 in the intermediate region runs completely free (that is to say also without substantial axial friction), only the torque for the screwing-in of the preforming region 101 is required for the further screwing-in of the screw 1 into the bone B. If slight additional friction still occurs, the torque required for the screwing-in will certainly increase, but to a considerably smaller extent than is the case with conventional screws.

In the event of the preforming region of the screw 1 having already entered the spongiosa and of the thread of the intermediate region running in a frictionless manner or only with slight friction, the torque required for the further screwing-in of the screw 1 can even become smaller. This is because the torque required for screwing the preforming region 101 into the spongiosa is lower than the torque which was required in order to screw the preforming region into the cortical substance, and the thread of the intermediate region 102 runs in a frictionless manner or only with slight friction. However, the requisite torque may increase again to a more pronounced extent when the screw is screwed in right up to the anchoring region 103, and the anchoring region 103 of the screw now comes into engagement with the bone B, because in this region the friction of the thread with the bone B increases again. In this case, the anchoring region 103 may in principle even be larger in outside diameter than the preforming region 101 in order to achieve especially effective anchoring of the screw 1 in the cortical substance of the bone B. This also applies analogously to the other exemplary embodiments of the screw according to the invention.

If the screw 1 has been largely screwed into the bone B (right-hand image in FIG. 5, illustration without bone plate), the anchoring region 103 of the screw 1 is effectively anchored in the cortical substance C (hard bone cortex), since the outside diameter OD of the screw 1 in the anchoring region 103 is of course the same size as or essentially the same size as the outside diameter OD of the preforming region 101 and is thus the same size as the diameter of the bone thread. The radial clearance there is thus zero or negligibly small. As an alternative to the spherical head 11 shown, the head of the screw may also be designed in such a way as described, for example, in WO 2004/086990, such that, for example, a bone plate can be fixed at a small distance from the bone (virtually as "fixateur interne"). This also applies analogously to the exemplary embodiments of the screw according to the invention that are explained below.

On the whole, this exemplary embodiment of the screw 1 according to the invention can be screwed into the bone B substantially more easily than conventional screws, thereby reducing the effort on the part of the surgeon, but in particular reducing the risk of a torsion fracture, in particular in the case of long and comparatively "thin" screws (that is to say, for example, in the case of screws for the oral and maxillofacial area having an outside diameter of 2.0 mm and length starting from 10 mm). When dimensioning the diameter of the core 100 of the shank 10—in particular in that section of the intermediate region which adjoins the preforming region—care is therefore always to be taken to ensure that the torque required for the screwing-in can always be reliably transmitted without it being possible for the screw to break (torsion fracture). That is to say that the core diameter CD in that section of the intermediate region 102 which directly adjoins the preforming region 101 cannot simply be reduced in any desired manner in order to reduce the friction and thus the additionally required torque during the further screwing-in, but rather care has to be taken to ensure that the requisite torque can always be reliably transmitted over the entire length of the shank 10.

Figure 6:
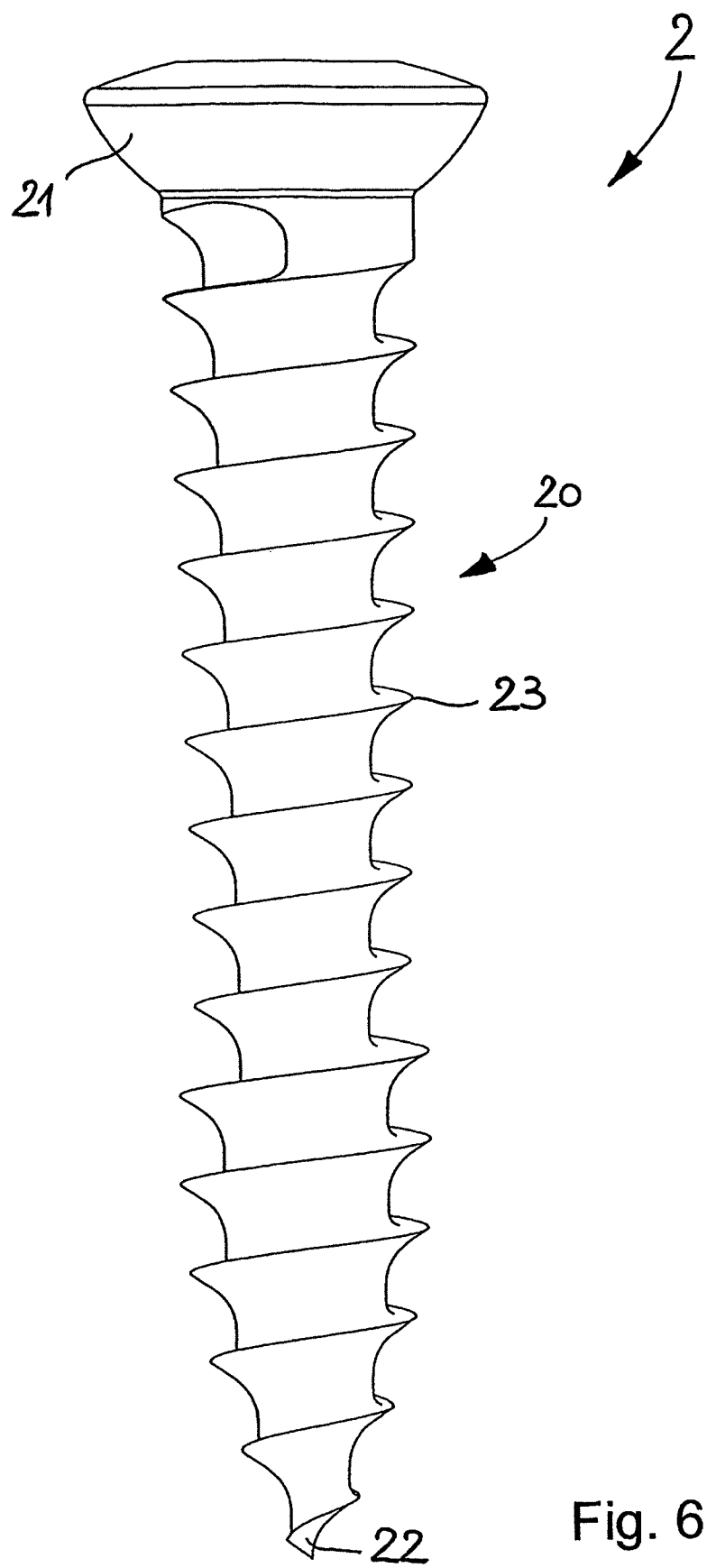
FIG. 6 shows a view of a second exemplary embodiment of the screw according to the invention.
Figure 7:
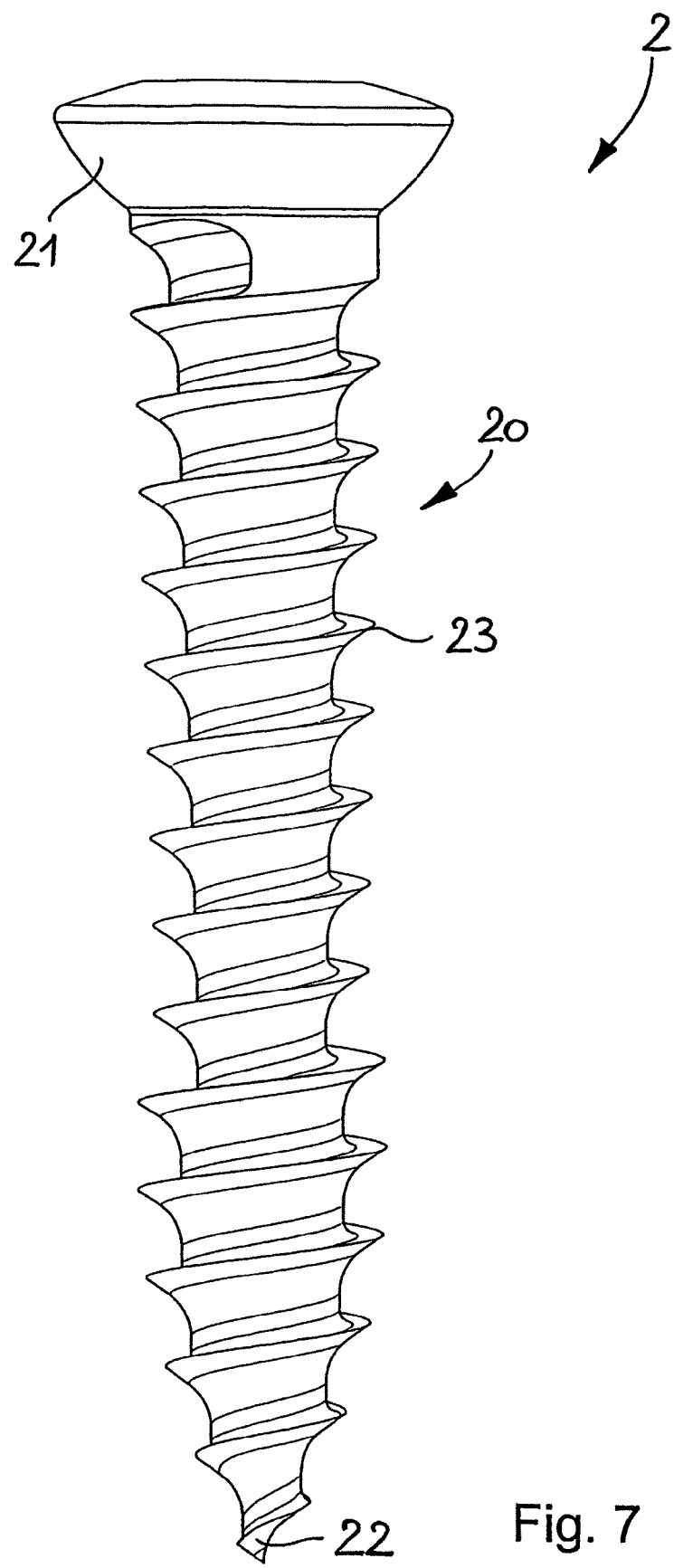
FIG. 7 shows the view from FIG. 6 with some auxiliary lines for better three-dimensional illustration of the screw.

A second exemplary embodiment of the screw according to the invention is explained below with reference to FIGS. 6 to 11. FIG. 6 shows a view of the second exemplary embodiment of the screw 2 according to the invention, once again a bone screw. The screw 2 comprises a shank 20 and a thread-free countersunk head 21, which, for example, enables it to be accommodated in a countersunk plate hole of a bone plate (not shown). The screw end 22 is designed as a point; the screw 2 shown in FIG. 6 is therefore a self-drilling (and of course also self-tapping) and self-centering screw. FIG. 7 shows the same screw, but with some additional auxiliary lines, thereby providing a better three-dimensional impression of the screw 2.

Figure 8:
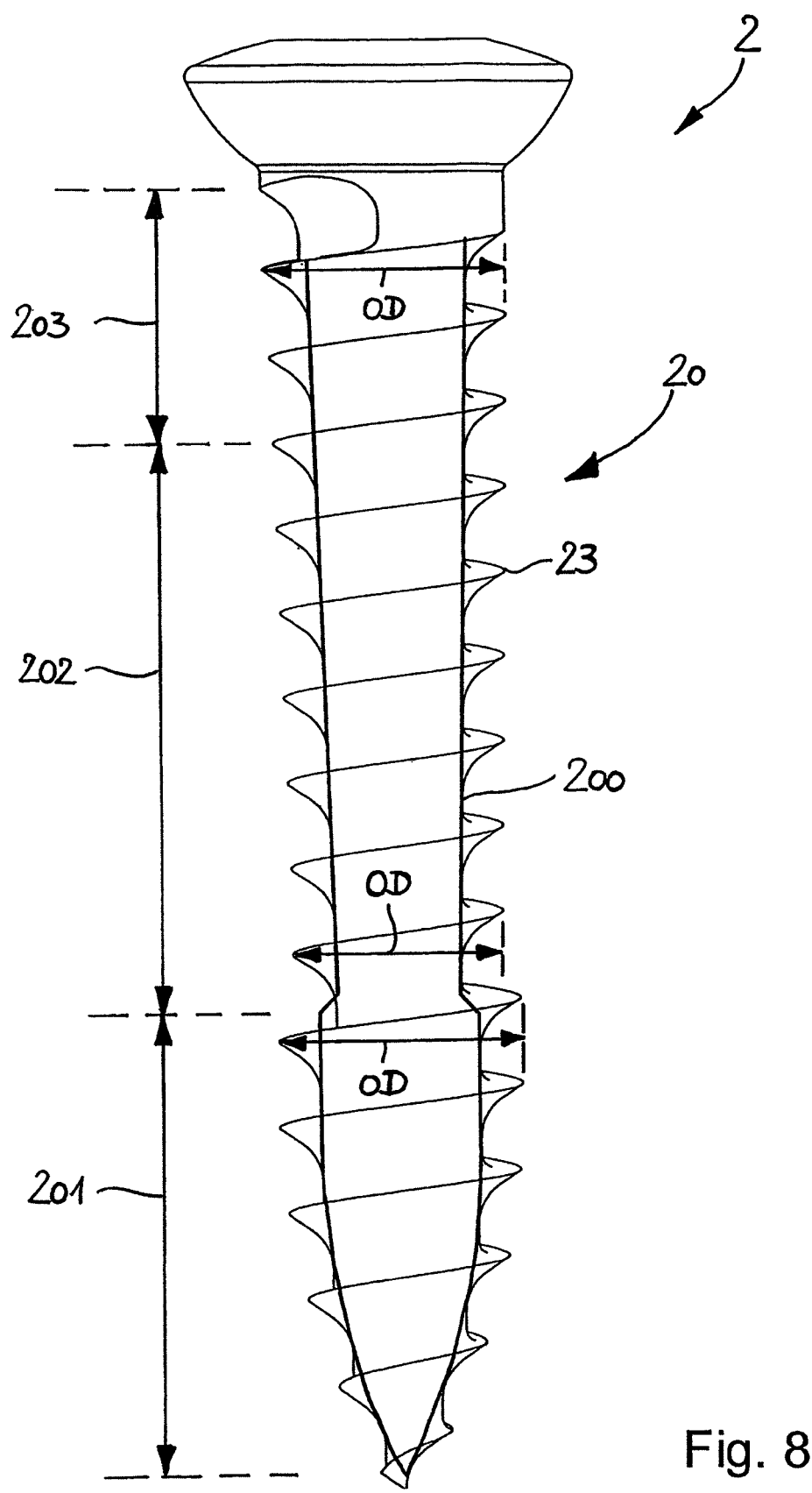
FIG. 8 shows a schematic illustration of the screw from FIG. 6 with exaggerated representation of the core of the screw shank.

The envelope over the thread 23 of the screw, which is designed here as a continuous thread of constant pitch, can be imagined with reference to FIG. 8, although in FIG. 8 the core 200 of the shank 20 is shown in exaggerated representation. Since the thread 23 again has a constant radial thread depth, the envelope (not shown), which represents the outside diameter of the screw, runs parallel to the core 200 of the shank 20 over the entire thread 23. The core 200 alone is shown schematically once again in FIG. 9.

The shank 20 again has three regions: a preforming region 201, an intermediate region 202 and an anchoring region 203, which regions can best be seen in the illustration in FIG. 8. In the preforming region 201, the outside diameter OD of the screw 2 increases from the point 22 up to that section which adjoins the intermediate region 202. In that section of the intermediate region 202 which directly adjoins this section of the preforming region 201, the outside diameter OD is smaller than in the preforming region 201. Starting from this section of the intermediate region 202 adjoining the preforming region 201, the outside diameter OD again increases conically across the intermediate region 202 and the anchoring region 203 until it is almost the same size as in the preforming region 201 at the start of the anchoring region 203 and is the same size as in the preforming region 201 at the top end of the anchoring region 203.

Figure 9:
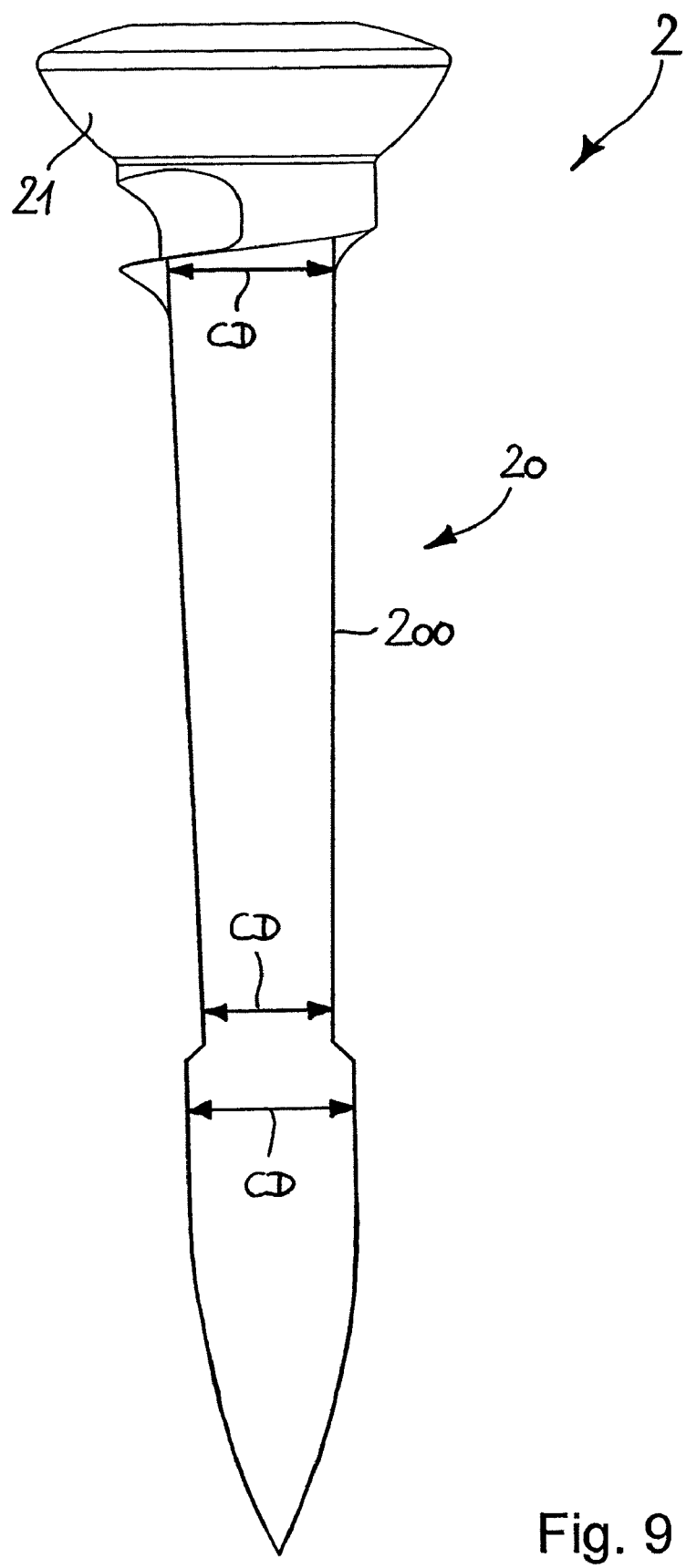
FIG. 9 shows a schematic illustration of the core of the screw shank of the screw from FIG. 6.

This analogously applies to the core diameter CD of the shank 20 (see FIG. 9). The core diameter CD is larger in that section of the preforming region which directly adjoins the intermediate region than in the directly adjoining section of the intermediate region, and starting from there it increases conically across the intermediate region and the anchoring region. In this application, the expression "conical" increase in the diameter is intended to mean, as shown here, rectilinearly conical increases in the diameter and also other profiles of the increase in the diameter, such as, for example, parabolic or hyperbolic increases in the diameter, increases in the diameter which follow a root function or other increases in the diameter.

Figure 10:
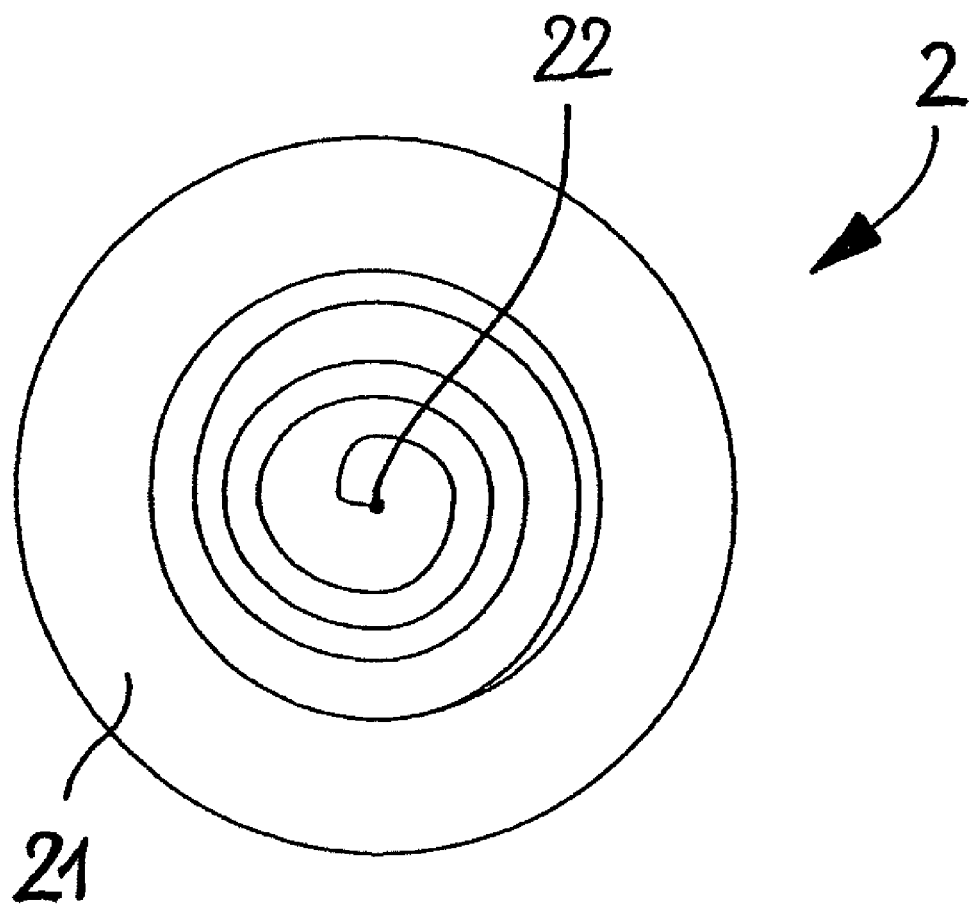
FIG. 10 shows a view of the screw from FIG. 6 from below.

FIG. 10 shows the screw 2 in a view from below, in which the increase in the outside diameter away from the point 22, until it reaches its maximum outside diameter in that section of the preforming region 201 (see FIG. 8) which adjoins the intermediate region 202, can readily be seen.

Figure 11:
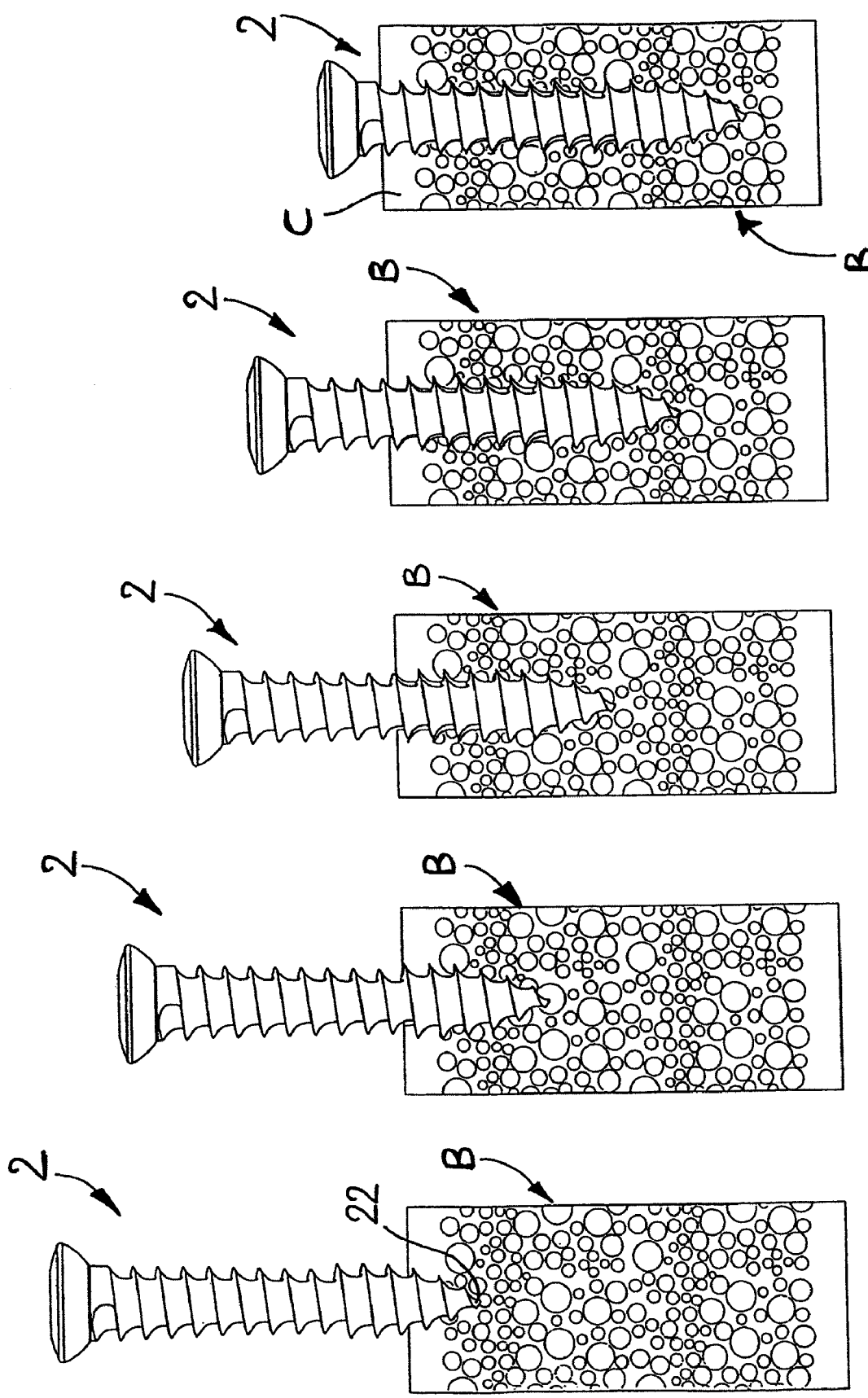

To screw in such a screw 2, which is self-drilling, the procedure is as shown in FIG. 11. First of all the screw 2 is placed with the point 22 onto the bone B and screwed in. The point 22 prevents the screw from slipping, and the small outside diameter of the screw in the immediate region of the point permits simple engagement of the screw in the bone B. A (pilot) hole is not produced, because the screw 2—as already stated—is self-drilling and also self-centering. After the screw engages, it is screwed in further in a manner similar to FIG. 5, and the comments made there therefore also apply to this second exemplary embodiment of the screw 2.

Figure 12:
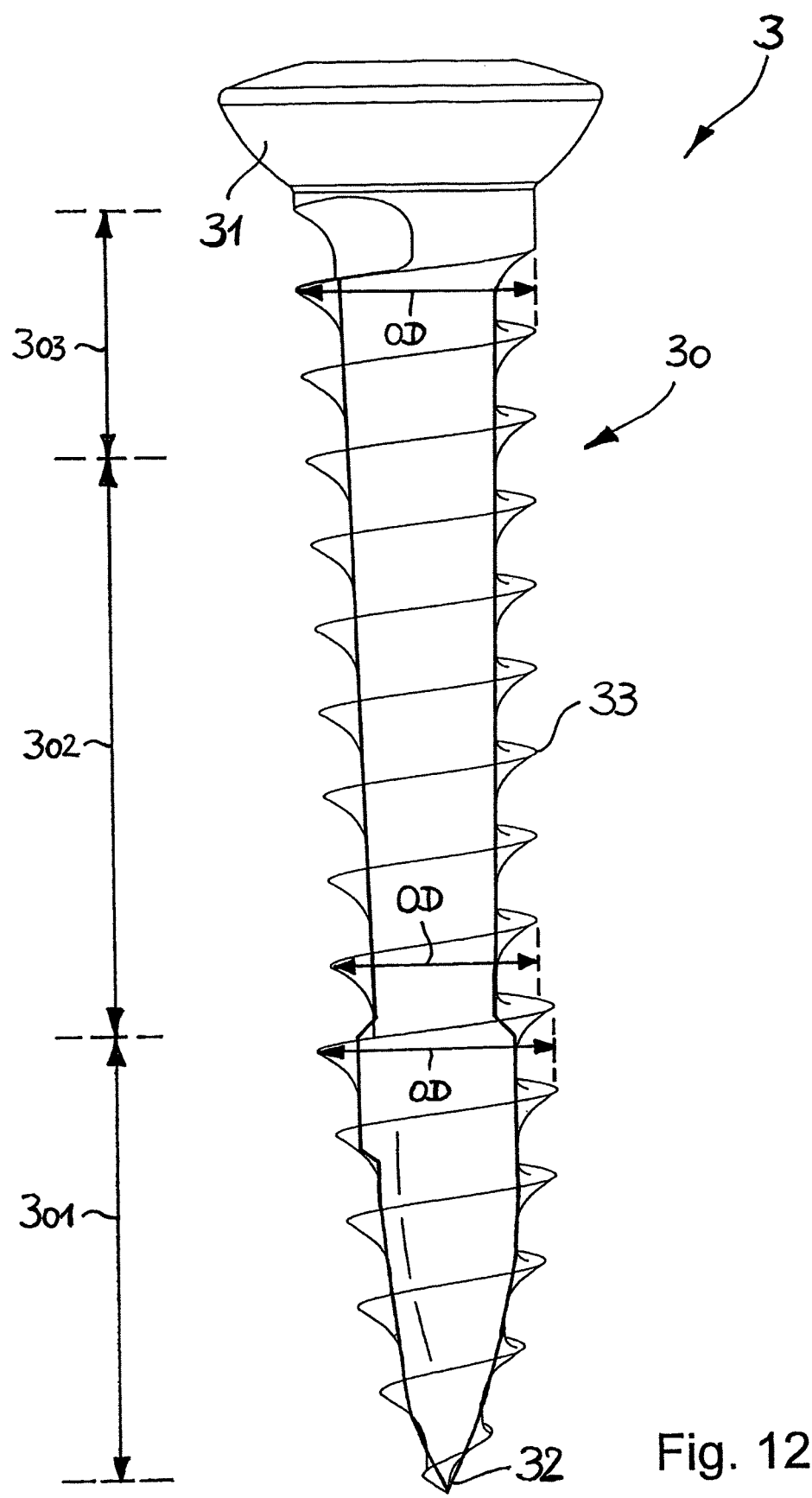
FIG. 12 shows a view of a third exemplary embodiment of the screw according to the invention.

A third exemplary embodiment of the screw according to the invention is explained below with reference to FIGS. 12 to 16. This third exemplary embodiment of the screw 3 according to the invention, once again a bone screw, is in some parts similar to the second exemplary embodiment of the screw 2 according to the invention, although the preforming region in the third exemplary embodiment of the screw 3 according to the invention is of different design. However, the screw 3 is in principle also a self-drilling (and of course also self-tapping) screw. FIG. 12 shows a view of the third exemplary embodiment of the screw 3 according to the invention—with exaggerated representation of the core of the screw shank. The screw 3 comprises a shank 30 and a thread-free spherical head 31, which, for example, enables it to be accommodated in a countersunk plate hole of a bone plate (not shown). The screw end 32 is designed as a point.

The envelope over the thread 33 of the screw, which is designed here as a continuous thread of constant pitch, can be imagined with reference to FIG. 12, although in FIG. 12 the core 300 of the shank 30 is shown in exaggerated representation. The core 300 alone is shown schematically once again in FIG. 13.

The shank 30 again has three regions: a preforming region 301, an intermediate region 302 and an anchoring region 303, which regions can be seen in FIG. 12. In the preforming region 301, however, the screw 3 is designed differently from the second exemplary embodiment of the screw 2 according to the invention, namely with a polygon-like cross section (also see FIG. 15), here a "curve of constant diameter" (which in FIG. 12 is indicated by the broken line in the preforming region). What is meant in principle by a "curve of constant diameter" can be better seen in FIG. 14 and will be explained in more detail. In that section of the preforming region 301 which directly adjoins the intermediate region 302, however, the preforming region is not designed as a curve of constant diameter, but rather in a similar manner as in the second exemplary embodiment of the screw according to the invention; it therefore has an outside diameter OD which is larger than the outside diameter OD of the directly adjoining section of the intermediate region 302. The outside diameter OD there is smaller than in the preforming region 301. Starting from this section of the intermediate region 302 adjoining the preforming region 301, the outside diameter OD again increases conically across the intermediate region 302 and the anchoring region 303 until it is almost the same size at the start of the anchoring region 303 as in that section of the preforming region 301 which adjoins the intermediate region 302 and is the same size at the top end of the anchoring region 303 as in that section of the preforming region 301 which adjoins the intermediate region 302.

Figure 13:
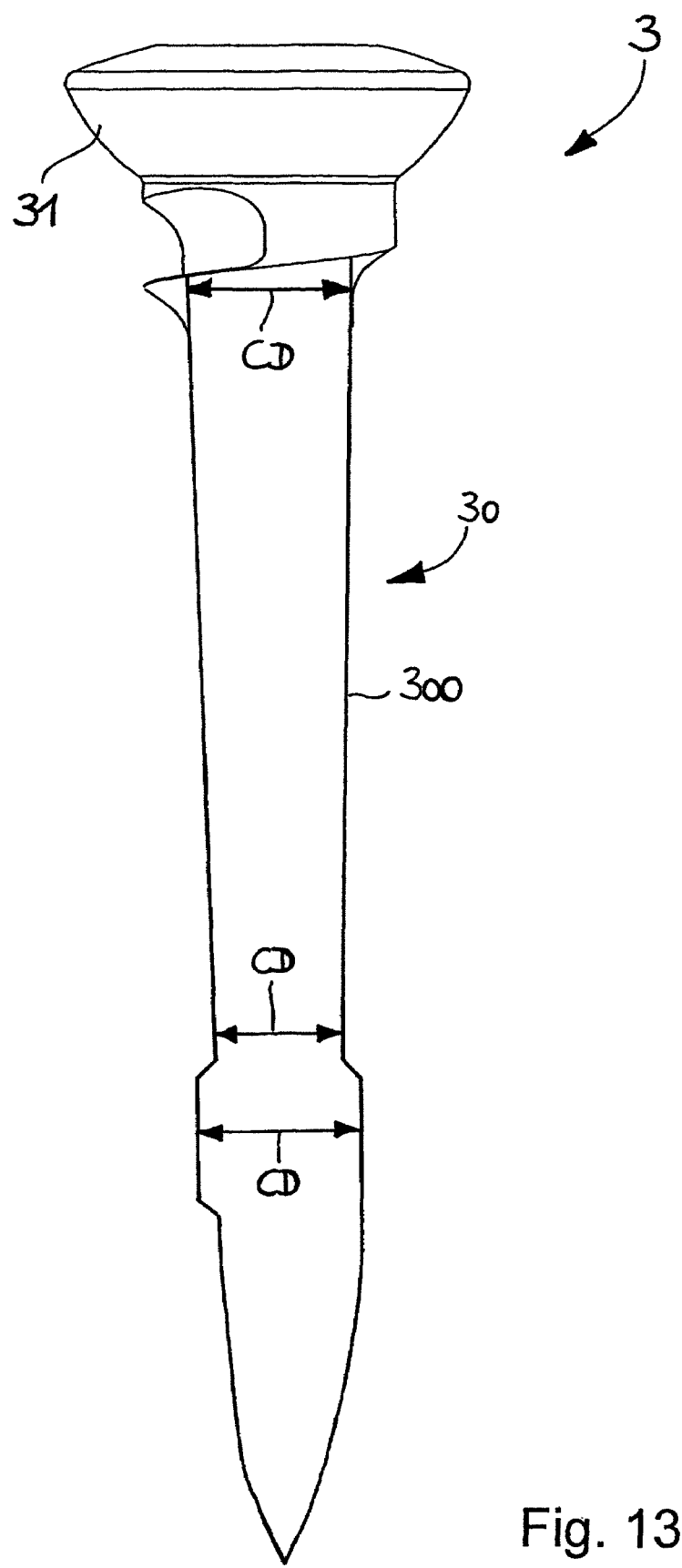
FIG. 13 shows a schematic illustration of the core of the screw shank of the screw from FIG. 12.

This analogously applies to the core diameter CD of the shank 30 (see FIG. 13). The core diameter CD is larger in that section of the preforming region which directly adjoins the intermediate region than in the directly adjoining section of the intermediate region, and starting from there it increases conically across the intermediate region and the anchoring region.

Figure 14:
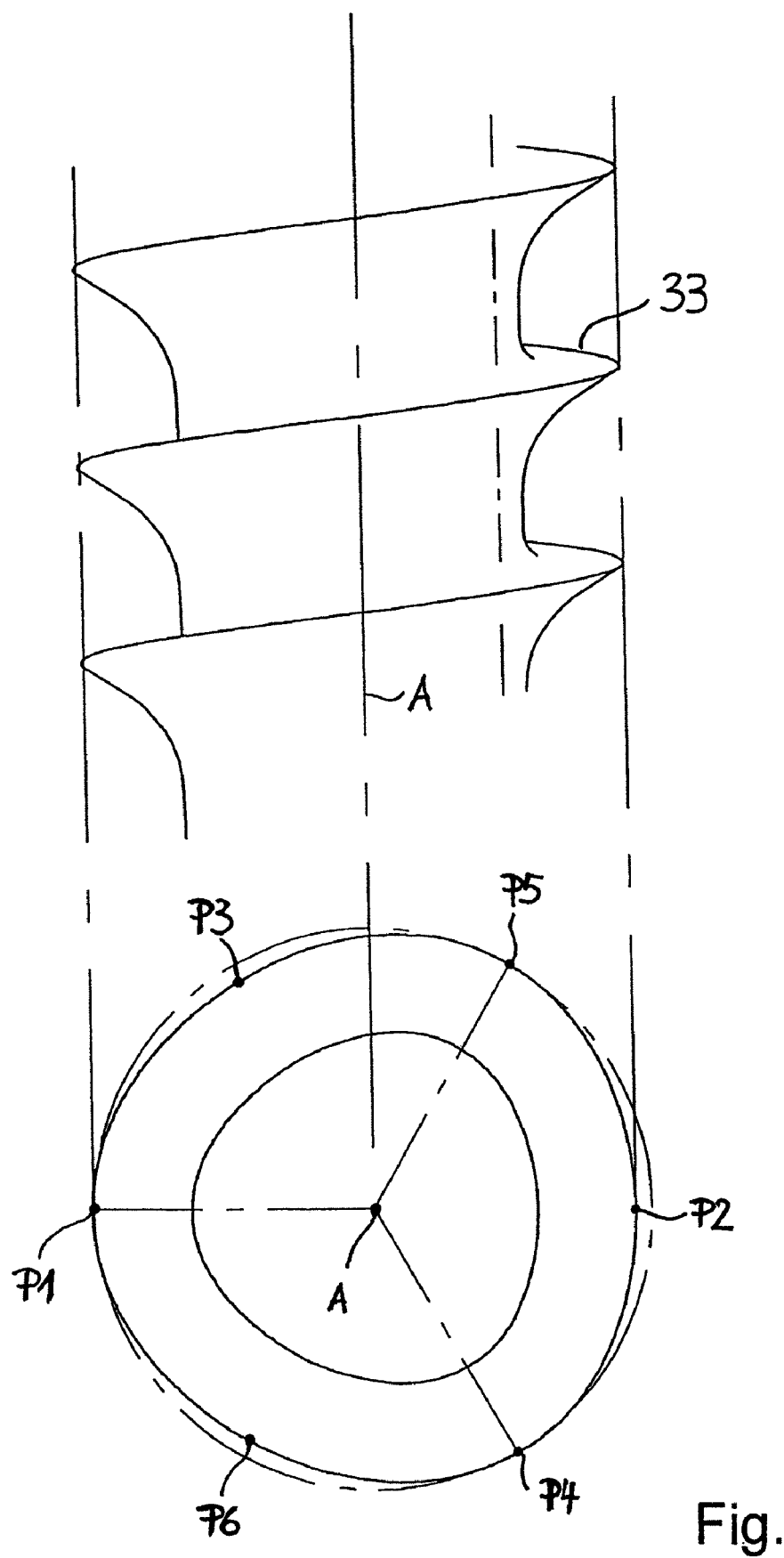
FIG. 14 shows a schematic view of a cross section through a "curve of constant diameter" and of an associated section of the preforming region in an elevation.

A "curve of constant diameter" is now shown in FIG. 14 in the bottom half, and a corresponding thread which follows the curve of constant diameter along its periphery is shown in the top half. The name "curve of constant diameter" for the cross-sectional shape of the shank in part of the preforming region results from the fact that the diameter at two opposite points which can be connected by a straight line through the screw axis A is always exactly the same size. Therefore the shank is always the same width with respect to two of such opposite points. This can be seen in FIG. 14 at the opposite points P1, P2 and P3, P4 and P5, P6. It can be seen here that the outer contour of the curve of constant diameter deviates from the circular shape, which is indicated by a broken line in FIG. 14 (bottom). The associated thread 33 is shown in the top half of FIG. 14. As can easily be seen from the bottom half of FIG. 14, there are in this case points P1, P4, P5 (or regions) which are at a maximum radial distance from the axis A of the screw 3 and regions which are at a smaller radial distance, e.g. the regions in which the points P2, P3, P6 lie. Radial engagement of the thread with the bone thus always takes place only at the points P1, P4, P5 (or in the regions directly adjacent to these points). The actual thread forming therefore takes place at these points or in these regions, and at the same time the axial surface pressure between screw and bone increases there. As a result, the preforming region 301 of the third exemplary embodiment of the screw 3 according to the invention can be screwed in even more easily than the preforming region 201 of the second exemplary embodiment of the screw 2 according to the invention.

Figure 15:
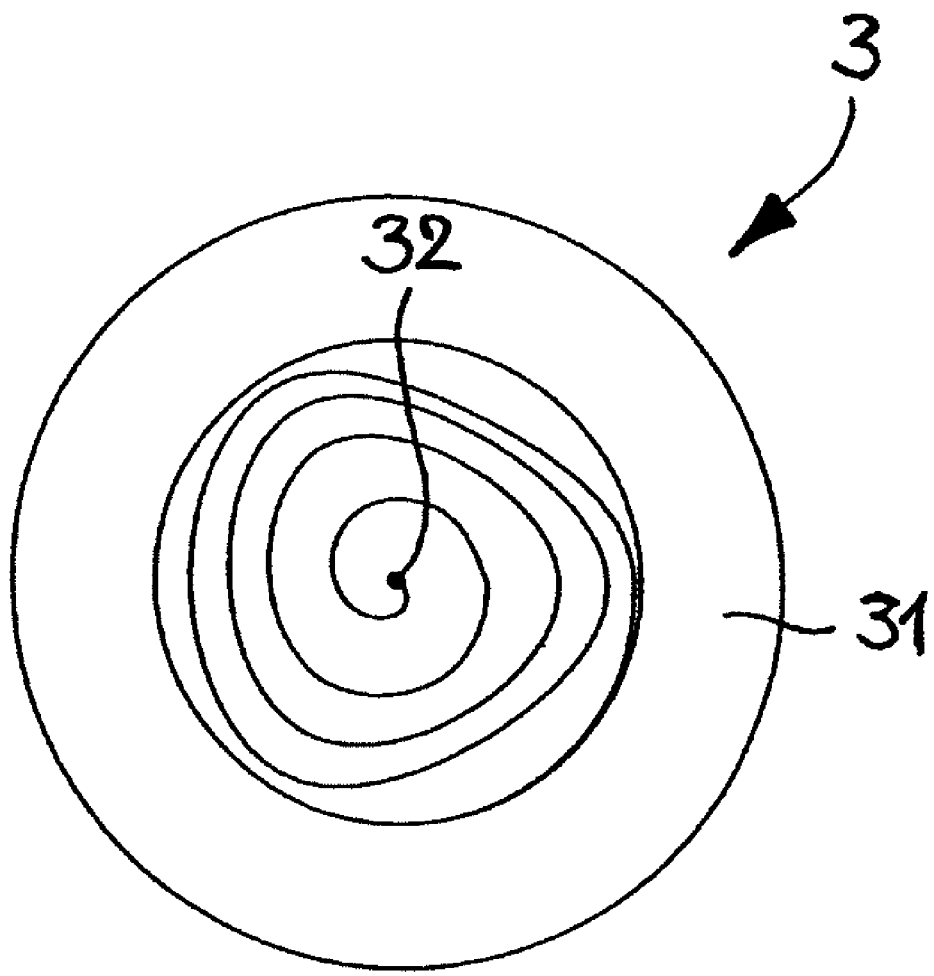
FIG. 15 shows a view of the screw from FIG. 12 from below.

FIG. 15 shows the screw 3 in a view from below, in which the curve of constant diameter away from the point 32 of the screw 3 can readily be seen, until the curve of constant diameter then adjoins, in the top section of the preforming region, a section of circular cross section.

Figure 16:
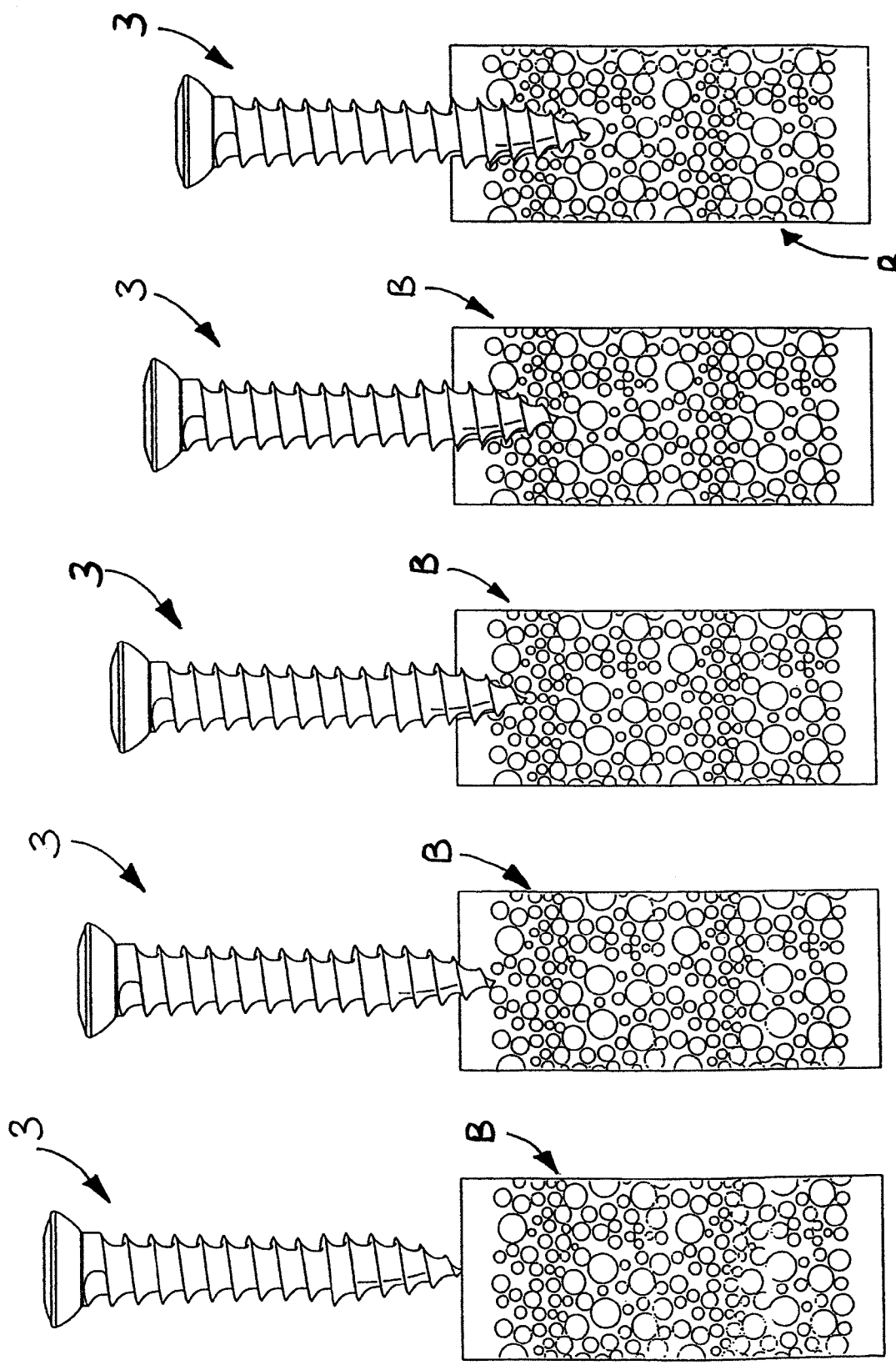

To screw in such a screw 3, which is self-drilling, the procedure is as shown in FIG. 16. With regard to the description, reference is essentially made here to FIG. 11. However, the difference when screwing in the preforming region is readily seen in FIG. 16: the regions whose radial distance from the screw axis is smaller (e.g. at the points P2, P3, P6) than the maximum radial distance (e.g. at the points P1, P4, P5) run free in the radial direction during the screwing-in. This can be seen especially effectively in the three right-hand images in FIG. 16.

It should also be mentioned that the curve of constant diameter is only one of the possible exemplary embodiments of such a polygon-like cross section—other forms are also suitable here (e.g. multi-angular, etc.), in which case the corners of the respective polygon may also be rounded, in a similar manner to the curve of constant diameter shown.

Figure 17:
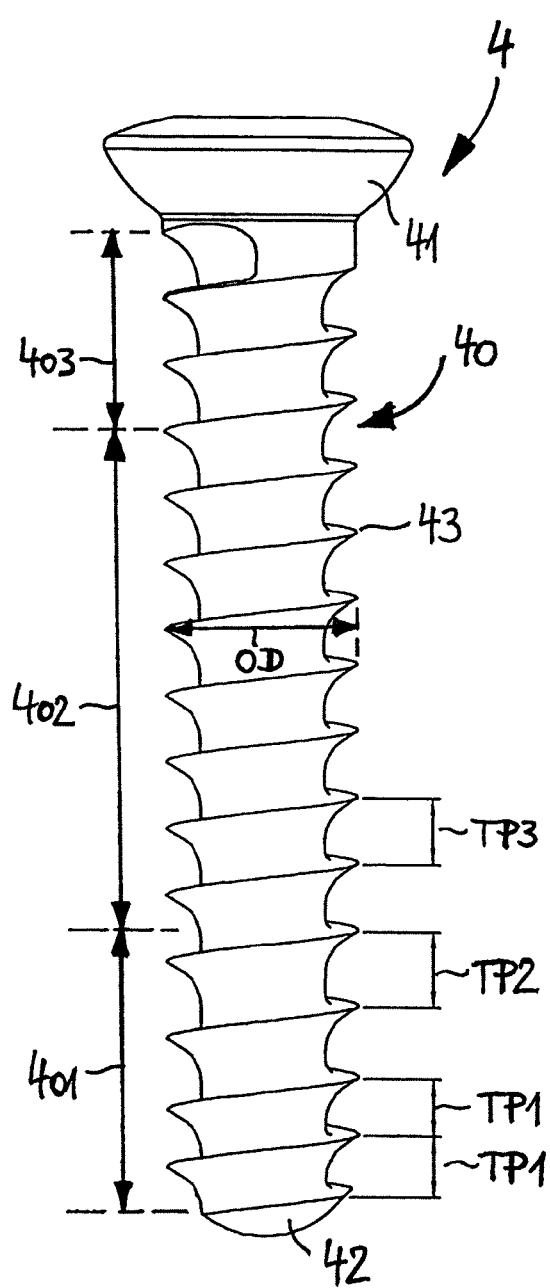
FIG. 17 shows a view of a fourth exemplary embodiment of the screw according to the invention.
Figure 18:
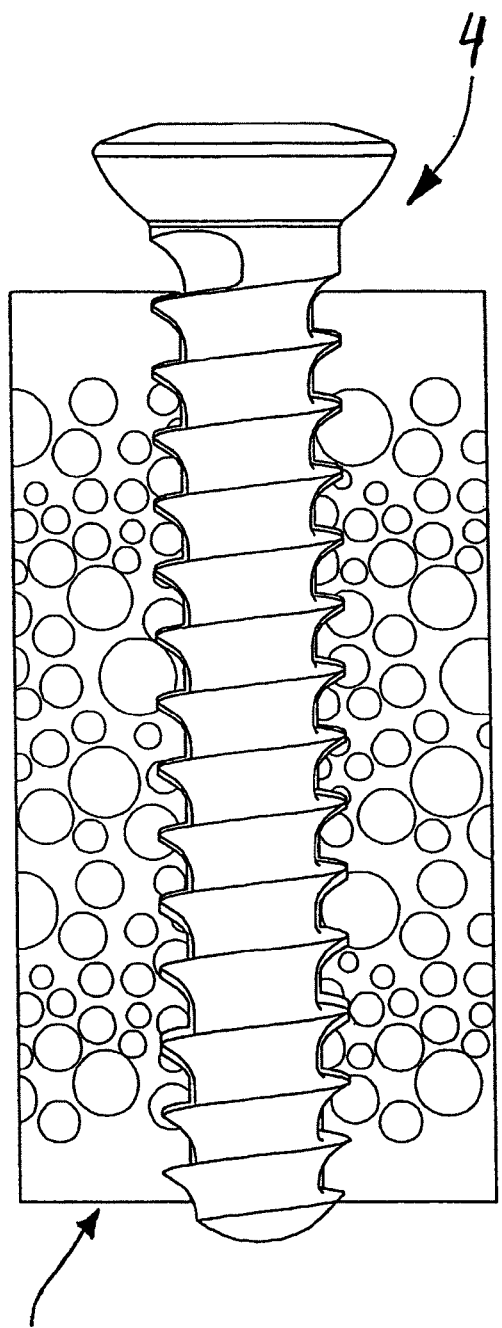
FIG. 18 shows a schematic illustration of the screw from FIG. 17 in the screwed-in state.

A fourth exemplary embodiment of the screw according to the invention is explained below with reference to FIGS. 17 and 18. FIG. 17 shows the first exemplary embodiment of the screw 4 according to the invention, once again a bone screw, in an elevation. The screw 4 comprises a shank 40 and a thread-free spherical head 41, which, for example, enables it to be accommodated in a countersunk plate hole of a bone plate (not shown). The screw end 42 is of blunt design; the screw 4 shown in FIG. 17 is therefore a self-tapping (not self-drilling) screw.

The envelope over the thread 43 of the screw, which is designed here as a continuous thread, runs in a circular-cylindrical manner; the screw therefore has a constant outside diameter OD over the entire length of the shank 40. The core diameter is likewise constant, such that the radial thread depth is constant.

The shank 40 has three regions: a preforming region 401, an intermediate region 402 and an anchoring region 403. In the preforming region 401, the thread 43 has a first thread pitch TP1 in a section arranged close to the screw end 42, whereas it has a second pitch TP2 in a section directly adjoining the intermediate region 402, this second pitch TP2 being larger than the first pitch TP1. In the intermediate region 402 and also in the anchoring region 403, the thread 43 then has a third thread pitch TP3 which is larger than the first thread pitch TP1 but smaller than the second thread pitch TP2.

To screw the screw 4 into the bone B, first of all a (pilot) hole has to be produced in the bone B, as already described with reference to FIG. 5, since the screw 4 is of course self-tapping but not self-drilling. When the preforming region 401 is being screwed in, first of all a bone thread having the pitch TP1 is formed by the section having the thread pitch TP1. After that, the section having the thread pitch TP2 is screwed in. The different thread pitches TP1 and TP2 are selected in such a way that an additional bone thread having the pitch TP2 is not cut, but rather the bone thread having the pitch TP1 is widened in the axial direction. That is to say that the two thread pitches TP1 and TP2 must not be greatly different from one another in any desired manner. The thread 43 of the intermediate region 402 and of the anchoring region 403 then slides into this axially widened bone thread formed by the preforming region 401. Since the thread pitch TP3 of the thread 43 there is larger than the thread pitch TP1 but smaller than the thread pitch TP2, the thread flanks of the intermediate region 402 and of the anchoring region 403 slide virtually without axial friction into the axially opened-out bone thread formed by the preforming region 401; they have a small axial clearance relative to the bone thread. This can be seen especially effectively in FIG. 18. Friction may certainly occur in the radial direction during the screwing-in, since the outside diameter OD of the screw 4 is constant over the entire length of the shank 40. Overall, however, the torque required for the screwing-in increases only marginally after the pre-forming region 401 has been completely screwed in; at any rate, it is substantially lower than the torque required for the screwing-in of conventional screws. This makes the screwing-in easier for the surgeon and also prevents the screw 4 from being able to break (torsion fracture). Despite the small axial clearance, the anchoring of the screw 4 in the bone B is effective. In addition, the bone can grow completely into the thread during the further course of healing and the axial clearance is thus eliminated again.

It should also be noted that, in transmucosal or transgingival applications of the screw according to the invention, a preferably amorphous (smooth) region of the screw may also be located between the head and the anchoring region, so that the head of the screw comes to lie outside the mucosa or gingiva. In this case, the amorphous (smooth) region reduces the risk of penetration of bacteria.

In addition, it should of course be noted that cutting grooves may also be provided in the preforming region away from the screw point. The transition between the preforming region and the intermediate region may also be designed to be somewhat "smoother" (less abrupt) than in the exemplary embodiments shown, which in particular may be advantageous with regard to subsequent unscrewing of the screw.

The screw according to the invention may of course also be cannulated in order to be guided, for example when being screwed in, along a guide wire introduced beforehand.

Single-start screws are shown in the exemplary embodiments described, but it is of course possible for the thread to be of multi-start design, in particular when the thread pitch is constant. In the case of multi-start threads, in particular two-start or three-start threads are suitable, but not exclusively. Screws having multi-start threads can lead to an even better fixation in the bone, because the thread crests or thread flanks in a multi-start thread (with respect to a specific azimuth plane perpendicular to the axis of the screw shank) are supported simultaneously at a plurality of points in the bone, a factor which leads to increased stability of the anchoring. For example, the thread crests in a two-start thread, with respect to a specific azimuth plane, are offset from one another by an azimuth angle of 180°. In a three-start screw, they are in each case offset by an azimuth angle of 120°.

Furthermore, the head of the screw may also be designed in such a way that it can be locked in the plate hole of a bone plate. An especially preferred type of such locking, which is certainly not the only possible locking, but is a preferred type of the locking, is described, for example, in WO 2004/086990.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A fixation-type thread-forming screw having a screw end, a shank and a thread-free head;
wherein the shank is provided with a thread and has a pre-forming region, an intermediate region, configured to follow the pre-forming region, and an anchoring region, configured to adjoin the intermediate region and below the head;
wherein the pre-forming region is arranged so as to directly adjoin the screw end, and wherein the pre-forming region, the intermediate region and the anchoring region are configured such that a continuous thread with a constant pitch extends along the pre-forming region, the intermediate region and the anchoring region;
wherein an outside diameter (OD) of the screw the screw in the pre-forming region, at least in a section adjoining the intermediate region, is larger than an outside diameter of the intermediate region, and the outside diameter at least in a part of the anchoring region is substantially the same diameter as or is larger than the outside diameter of a section of the pre-forming region that adjoins the intermediate region, so that when the pre-forming region is screwed in during a first screwing-in phase, the torque required for tightening increases at a first torque rate until a first torque level has been reached, until the pre-forming region has been completely screwed in, and wherein irrespective of the material into which the screw is screwed-in said first torque rate increases during the first screwing-in phase, so that after the pre-forming region has been completely screwed in during the first screwing-in phase, thereafter, during a second screwing in phase, the torque required for tightening increases at a second torque rate, wherein the second torque rate corresponds to either no increase in torque or a slight increase in torque relative to the first torque rate.

2. The thread-forming screw according to claim 1, wherein the screw end is blunt and the outside diameter (OD) is constant in the pre-forming region and is smaller in the intermediate region in a section directly adjoining the pre-forming region than the outside diameter of the pre-forming region, and in which screw the outside diameter, starting from this section of the intermediate region adjoining the pre-forming region, increases conically across the intermediate region and the anchoring region until, in the anchoring region, it is the same size as or larger than the outside diameter of the pre-forming region.

3. Thread-forming screw as claimed in claim 1, wherein the screw is produced from a biocompatible material, the biocompatible material selected from the group consisting of titanium, a titanium alloy, or a bio-resorbable material.

4. A fixation-type thread-forming screw having a screw end, a shank and a thread-free head;
wherein the shank is provided with a thread and has a pre-forming region, an intermediate region, configured to follow the pre-forming region, and an anchoring region, configured to adjoin the intermediate region and below the head;
wherein the pre-forming region is arranged so as to directly adjoin the screw end, and wherein the pre-forming region, the intermediate region and the anchoring region are configured such that a continuous thread with a constant pitch extends along the pre-forming region, the intermediate region and the anchoring region;
wherein an outside diameter (OD) of the screw in the pre-forming region, at least in a section adjoining the intermediate region is larger than an outside diameter of the intermediate region, and the outside diameter at least in a part of the anchoring region is substantially the same diameter as or is larger than the outside diameter of a section of the pre-forming region that adjoins the intermediate region, so that when the pre-forming region is screwed in during a first screwing-in phase, the torque required for tightening increases at a first torque rate until a first torque level has been reached, until the pre-forming region has been completely screwed in, and wherein irrespective of the material into which the screw is screwed-in, said first torque rate increases during the first screwing-in phase, so that after the pre-forming region has been completely screwed in during the first screwing-in phase, thereafter, during a second screwing-in phase, the torque required for tightening increases at a second torque rate, wherein the second torque rate corresponds to either no increase in torque or a slight increase in torque relative to the first torque rate; and
wherein the screw end has a pointed end and the outside diameter (OD) of the pre-forming region increases starting from the pointed end up to a section which directly adjoins the intermediate region, and the outside diameter of the intermediate region is smaller in a section directly adjoining the pre-forming region than the outside diameter of the adjoining section of the pre-forming region, and in which screw the outside diameter, starting from this section of the intermediate region adjoining the pre-forming region, increases conically across the intermediate region and the anchoring region until, at least in a part of the anchoring region, it is substantially the same size or is larger than the outside diameter of the pre-forming region in the section adjoining the intermediate region.

5. Thread-forming screw according to claim 4, wherein the screw shank in the pre-forming region has a polygon-like cross section which has points or regions which are at a maximum radial distance from a screw axis and regions which are at a smaller radial distance from the screw axis than those points or regions which are at a maximum radial distance from the screw axis.

6. Thread-forming screw according to claim 4, wherein a core diameter (CD) of the screw shank is smaller in the intermediate region than in that section of the pre-forming region which adjoins the intermediate region, and in which, in that part of the anchoring region whose outside diameter is the same size as or essentially the same size as or is larger than that section of the pre-forming region which adjoins the intermediate region, the core diameter of the screw shank is the same size as or essentially the same size as or is larger than the core diameter of that section of the pre-forming region which adjoins the intermediate region.

7. A fixation-type thread-forming screw having a screw end, a shank and a thread-free head;
wherein the shank is provided with a thread and has a pre-forming region, an intermediate region, configured to follow the pre-forming region, and an anchoring region, configured to adjoin the intermediate region and below the head
wherein the pre-forming region is arranged so as to directly adjoin the screw end, and wherein the pre-forming region, the intermediate region and the anchoring region are configured such that a continuous thread with a constant pitch extends along the pre-forming region, the intermediate region and the anchoring region:
wherein an outside diameter (OD) of the screw in the pre-forming region, at least in a section adjoining the intermidate region, is larger than an outside the intermediate region, and the outside diameter at least an a part of the anchoring region is substantially the same diameter as or is larger than the outside diameter of a section of the pre-forming region that adjoins the intermediate region, so that when the pre-forming region is screwed in during a first screwing-in phase, the torque required for tightening increases at a first torque rate until a first torque level has been reached, until the pre-forming region has been completely screwed in, and wherein irrespective of the material into which the screw is screwed-in, said first torque rate increases during the first screwing-in phase, so that after the pre-forming region has been completely screwed in during the first screwing-in phase, thereafter, during a second screwing-in phase, the torque required for tightening increases at a second torque rate, wherein the second torque rate corresponds to either no increase in torque or a slight increase in torque relative to the first torque rate: and
wherein the screw shank in the pre-forming region has a polygon-like cross section which has points or regions which are at a maximum radial distance from a screw axis and regions which are at a smaller radial distance from the screw axis than those points or regions which are at a maximum radial distance from the screw axis.

8. Thread-forming screw according to claim 7, wherein the screw shank in the pre-forming region is curved and has a constant diameter.

9. A fixation-type thread-forming screw having a screw end, a shank and a thread-free head;
wherein the shank is provided with a thread and has a pre-forming region, an intermediate region, configured to follow the pre-forming region, and an anchoring region, configured to adjoin the intermediate region and below the head;
wherein the pre-forming region is arranged so as to directly adjoin the screw end, and wherein the pre-forming region, the intermediate region and the anchoring region are configured such that a continuous thread with a constant pitch extends along the pre-forming region, the intermediate region and the anchoring region.
wherein an outside diameter (OD) of the screw in the pre-forming region, at least in a section adjoining the intermediate region, is larger than an outside diameter of the intermediate region, and the outside diameter at least in a part of the anchoring region is substantially the same diameter as or is larger than the outside diameter of a section of the region that adjoins the intermediate region, so that when the pre-forming region is screwed in during a first screwing-in phase, the torque required for tightening increases at a first torque rate until a first torque level has been reached, until the pre-forming region has been completely screwed in, and wherein irrespective of the material into which the screw is screwed-in, said first torque rate increases during the first screwing-in phase, so that after the pre-forming region has been completely screwed in during the first sere thereafter, during a second screwing in phase, the torque required for tightening increases at a second torque rate, wherein the second torque rate corresponds to either no increase in torque or a slight increase in torque relative to the first torque rate, and wherein a core diameter (CD) of the screw shank is smaller in the intermediate region than in that section of the pre-forming region which adjoins the intermediate region, and in which, in that part of the anchoring region whose outside diameter is the same size as or essentially the same size as or is larger than that section of the pre-forming region which adjoins the intermediate region, the core diameter of the screw shank is the same size as or essentially the same size as or is larger than the core diameter of that section of the pre-forming region which adjoins the intermediate region.

10. A fixation-type thread-forming screw having a screw end, a shank and a thread-free head;

wherein the shank is provided with a continuous thread and has a pre-forming region, an intermediate region, which is arranged to follow the pre-forming region, and an anchoring region, which is arranged so as to adjoin the intermediate region and below the head:, wherein the pre-forming region is arranged so as to directly adjoin the screw end, and wherein the screw shank has a constant outside diameter in the pre-forming region and in the intermediate region, and is provided in the pre-forming region with a thread having different itches, a first in a section arranged close to the screw1 and a second pitch in a section directly adjoining the intermediate region, the second pitch being larger than the first pitch, and in which the screw shank in the anchoring region is provided with a thread having a third pitch which is larger than the first pitch and smaller than the second pitch of the thread in the pre-forming region so that when the pre-forming region is screwed in during a first screwing-in phase, torque required for tightening increases at a first torque rate until a first torque level has been reached, until the pre-forming region has been completely screwed in, and wherein irrespective of the material into which the screw is screwed-in, said first torque rate increases during the first screwing-in phase, so that after the pre-forming region has been completely screwed in during the first screwing-in phase, thereafter, during a second screwing-in phase. the torque required for tightening increases at a second torque rate, wherein the second torque rate corresponds to either no increase in torque or a slight increase in torque relative to the first torque rate.

11. Thread-forming screw according to claim 10, wherein the screw is provided in the intermediate region with a thread whose pitch corresponds to the third pitch of the thread in the anchoring region.

\* \* \* \* \*

UNITED STATES PATENT AND TRADEMARK OFFICE
CERTIFICATE OF CORRECTION

PATENT NO. : 8,403,972 B2  
APPLICATION NO. : 12/091137  
DATED : March 26, 2013  
INVENTOR(S) : Alain Hasenböhler et al.

Page 1 of 2

It is certified that error appears in the above-identified patent and that said Letters Patent is hereby corrected as shown below:

In the Claims

In column 12, claim 1, line 32, after "(OD) of the screw" delete "the screw".

In column 13, claim 4, line 16, immediately after "intermediate region" insert --,--.

In column 14, claim 7, line 7, immediately after "below the head" insert --;--.

In column 14, claim 7, line 13, immediately after "anchoring region" replace ":" with --;--.

In column 14, claim 7, line 16, replace "intermidate region, is larger than an outside the" with --intermediate region, is larger than an outside diameter of the--.

In column 14, claim 7, line 17, after "diameter at least" replace "an a" with --in a--.

In column 14, claim 9, line 56, immediately after "the anchoring region" replace "." with --;--.

In column 14, claim 9, line 63, before "region that adjoins" insert --pre-forming--.

In column 15, claim 9, line 6, before "thereafter, during" replace "sere" with --screwing-in phase,--.

In column 15, claim 10, line 28, immediately after "and below the head" replace ":," with --;--.

In column 16, claim 10, line 3, after "having different" replace "itches" with --pitches--.

In column 16, claim 10, line 4, before "in a section arranged" insert --pitch--.

Signed and Sealed this  
Eighteenth Day of March, 2014

Michelle K. Lee  
*Deputy Director of the United States Patent and Trademark Office*

CERTIFICATE OF CORRECTION (continued)
U.S. Pat. No. 8,403,972 B2

In the Claims (cont'd)

In column 16, claim 10, line 4, after "close to the" replace "screw1" with --screw end--.

In column 16, claim 10, line 12, before "torque required for" insert --the--.

UNITED STATES PATENT AND TRADEMARK OFFICE
CERTIFICATE OF CORRECTION

PATENT NO. : 8,403,972 B2  Page 1 of 1
APPLICATION NO. : 12/091137
DATED : March 26, 2013
INVENTOR(S) : Hasenböhler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 605 days.

Signed and Sealed this
First Day of September, 2015

Michelle K. Lee
*Director of the United States Patent and Trademark Office*